United States Patent [19]

Tripp

[11] Patent Number: 4,700,577

[45] Date of Patent: Oct. 20, 1987

[54] QUALITY CONTROL FOR SUCKER RODS

[75] Inventor: Harley A. Tripp, Houston, Tex.

[73] Assignee: Shell Oil Company, Houston, Tex.

[21] Appl. No.: 917,282

[22] Filed: Oct. 9, 1986

Related U.S. Application Data

[63] Continuation of Ser. No. 619,508, Jun. 11, 1984, abandoned.

[51] Int. Cl.[4] .......................... G01N 3/08; G01H 1/00
[52] U.S. Cl. ........................................ 73/801; 73/789; 73/827
[58] Field of Search ................. 73/587, 789, 791, 801, 73/826, 827, 795, 796

[56] References Cited

U.S. PATENT DOCUMENTS

| | | | |
|---|---|---|---|
| 3,313,147 | 4/1967 | Rebbeck | 73/791 |
| 4,317,368 | 3/1982 | McElroy | 73/587 |
| 4,475,404 | 10/1984 | Rutledge et al. | 73/827 |
| 4,480,482 | 11/1984 | Henry et al. | 73/789 |

*Primary Examiner*—John Chapman

[57] ABSTRACT

A method for testing fiberglass sucker rods wherein the rod is pulled to a predetermined stress level while measuring the load, elongation and acoustic emissions. The load versus displacement is plotted in real time while the measured values are used to calculate the modulus of elasticity for various load ranges. From the measurements and calculated modulus of elasticity the quality of the rod can be determined.

3 Claims, 3 Drawing Figures

QUALITY CONTROL FOR SUCKER RODS

This is a continuation of application Ser. No. 619,508, filed June 11, 1984, abandoned.

BACKGROUND OF THE INVENTION

The present invention relates to the production of crude oil wherein beam pumping units are used to actuate downhole pumps to lift the crude to the surface. Sucker rods are used to couple the beam pumping unit at the surface to the reciprocating pump located at the bottom of the well. Sucker rods are conventionally provided with male threads at each end and are coupled together by coupling units to form a continuous rod from the surface to the bottom of the well. Normally, the sucker rods are made of steel and provided with suitable threaded ends and flat sections to permit the use of wrenches in coupling the rods together. While steel rods are satisfactory, in some installations it would be desirable to use rods formed from non-corroding materials. This is especially the case when producing wells that contain sour crude, that is, crude having a high sulfur content that corrodes the rods and increases the maintenance required for the pumping unit.

In order to overcome the problem of corrosion in sour wells it has been suggested that fiberglass rods be used. Fiberglass rods consist of a thermosetting resin, either a polyester type resin or an epoxy type resin and reinforcing fiber materials. The most often used fiber reinforcing material is continuous lengths of glass fibers since they provide high strength at a relatively low cost. Other fiber such as graphite or boron could also be used but their high cost results in a relatively high priced sucker rod. Fiber reinforced plastic sucker rods are normally formed by extruding a continuous length of the fiber filament reinforcing material impregnated with a suitable thermosetting resin. The rods are made in relatively long lengths and then trimmed to the desired overall length and provided with threaded end fittings that are normally attached to the rod by an adhesive. The end fittings are made from steel or similar metals to withstand the wear of making up the rod string and disassembling it. The adhesive is normally epoxy and after the epoxy has cured, the rods are test pulled to some preset limit, normally one-half their ultimate strength, to ensure that the threaded ends are firmly attached to the rod. In the past the sole criteria for these tests has been either the rod failed if the end separated from the rod, or it passed the test. No attempt was made to evaluate the quality of the rod or the integrity of the joint between the end fitting and the rod body. This resulted in a large number of fiber reinforced resin type rods passing the initial test, yet failing in service by pulling off the end fitting or failure of the fiber reinforced plastic laminate itself.

SUMMARY OF THE INVENTION

The present invention solves the above problems by providing a testing procedure that accurately evaluates the overall quality of the rod, even though the rod may pass the previously used test. In particular, the rod is pulled in tension to approximately one-half of its ultimate strength while measuring the load, elongation and acoustic emissions from the rod. The measurements are controlled by a monitoring system which may be controlled by a properly programmed small computer. The monitoring system samples the load on the rod and its elongation several times a second while accumulating a total count of the acoustic emissions from the rod.

During the test, the acoustic emissions are caused by individual fiberglass strands breaking within the rod as the load on the rod is increased and provides a measurement of the quality of the rod laminate. From the measured load and elongation data the modulus of elasticity of the rod is calculated over two different load ranges and the difference between the two calculated values is related to the quality of the rod. Any difference in the modulus elasticity is caused either by the epoxy used to attach the metal end fittings to the rod or by a slipping of the metal end fitting on the rod. In either case, it is an indication that the rod end will probably fail in service and the rod should be rejected or discarded.

BRIEF DESCRIPITON OF THE DRAWINGS

The present invention will be more easily understood from the following description of a preferred embodiment when taken in conjunction with the attached drawings in which.

DESCRIPTION OF THE PREFERRED EMBODIMENTS

Figure 1:
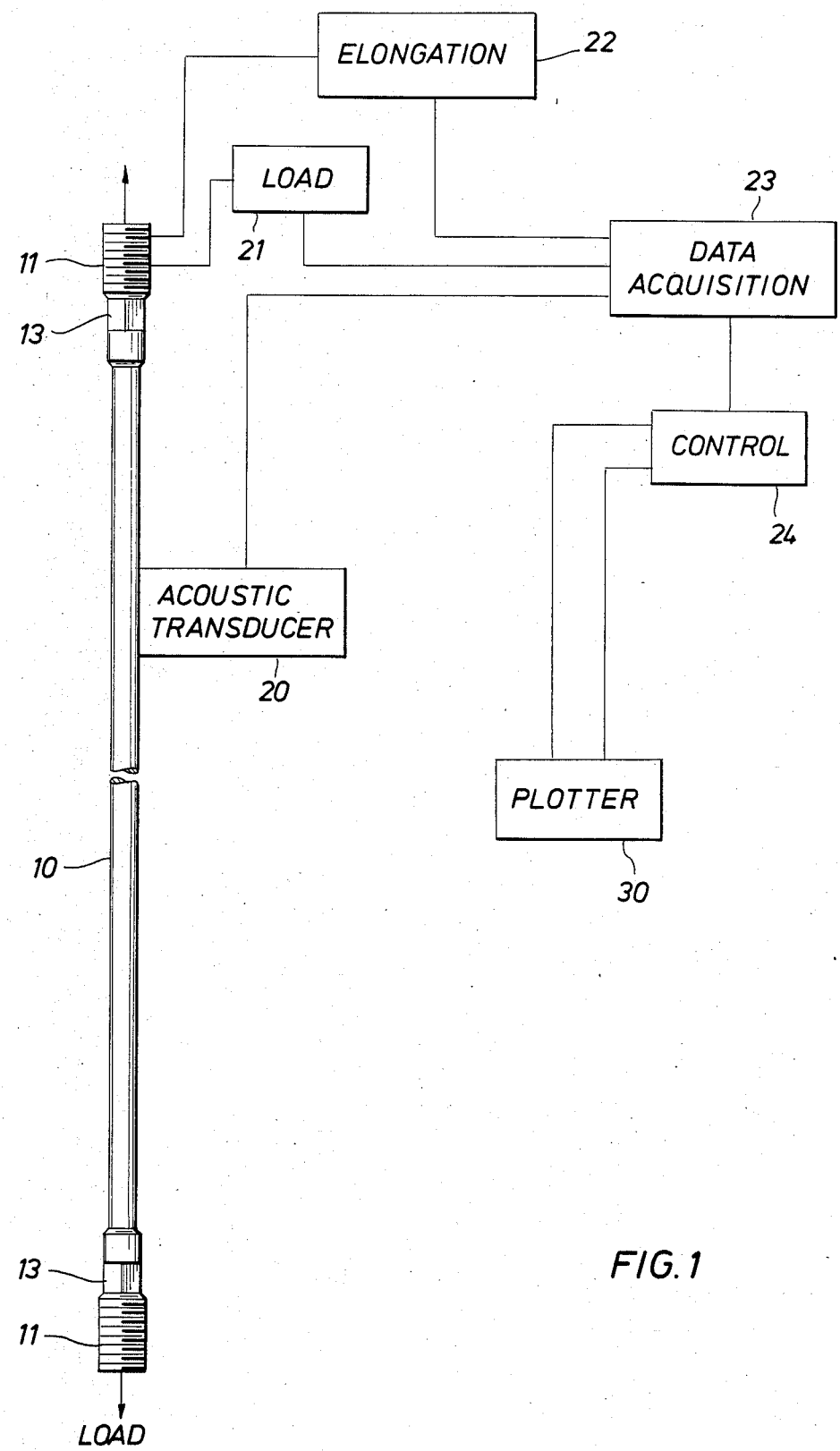
FIG. 1 is a block diagram of equipment suitable for making the required measurements on a sucker rod.

Referring now to FIG. 1 there is shown a block diagram of the system suitable for acquiring the data necessary for determining the quality of a fiberglass sucker rod. In particular, there is shown a fiberglass sucker rod having metal end fittings 11 secured to each end. The metal end fittings comprise a threaded portion and a square portion 13 that can be used as a wrench flat to hold the rods as they are joined together by the threaded couplings. The metal ends are attached to the rod by an epoxy resin which is allowed to cure to firmly anchor the metal end fittings to the rods. Various means may be used to increase the bond between the metal end fittings and the rods, for example, undercut sections in the metal end fittings assist in anchoring the ends to the rods.

After the epoxy has been cured so that the end fittings are firmly attached to the rod, it is placed in a suitable tensile testing machine. Various types of testing machines are available commercially which will apply a tensile load to a rod-like member while measuring both the load applied and the elongation of the member under test. Further, these machines can be controlled so that the load is applied at a constant rate, which rate can be varied if one so desires.

An acoustic transducer 20 is coupled to the rod by a suitable means to measure the acoustic emissions from the rod. The transducer may comprise a piezoelectric crystal type transducer such as a microphone coupled by suitable material and firmly clamped to the rod. Also, a transducer 21 is used to measure the load applied to the rod and a transducer 22 to measure the elongation of the rod as the loads are coupled to the rod. Normally, the load and elongation transducers will be part of the testing equipment and need not be separately attached to the rod. The data measured by the transducers is sampled by a data acquisition system 23 which is controlled by controller 24. The controller 24 may comprise a conventional small computer that is programmed to signal each of the transducers when it is desired to make a measurement. The measurements made by the transducers are recorded in the computer memory using the data acquisition system and may be displayed on a CRT screen. This display may then be printed on a digital printer/plotter 31 connected to the computer.

Figure 2:
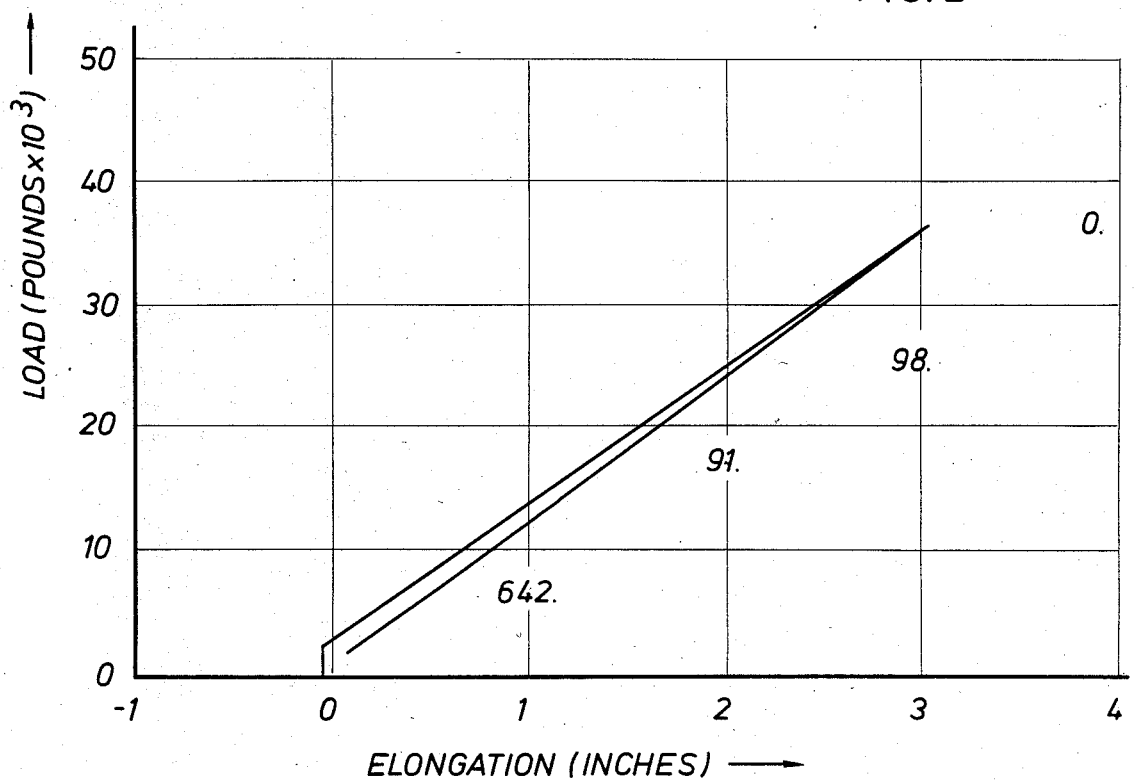
FIG. 2 is a plot of the load versus elongation for an actual rod.
Figure 3:
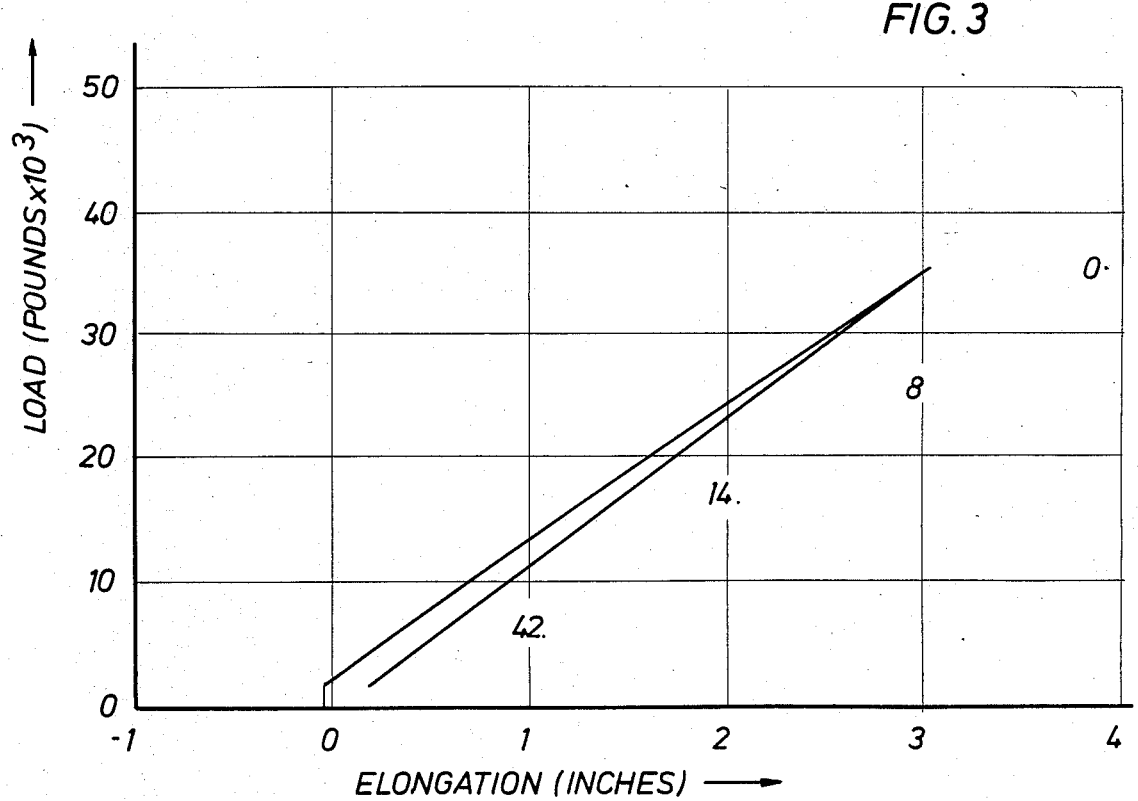
FIG. 3 is a similar plot for a second rod.

Referring to FIGS. 2 and 3 there is shown representative examples of the data recorded in the computer and printed using printer/plotter 31 while testing actual sucker rods. In particular, the data displayed is the load applied to the rod versus elongation, while the total acoustic counts are indicated by the numbers alongside the load/elongation curves. The modulus of elasticity is calculated for the data shown in FIG. 2 for two load ranges; the first 10-30,000 lbs. and the second 30-35,948 lbs. The first load range provided a modulus of 6.770 $10^6$ psi while the second provided a modulus of 6.671 $10^6$ psi. The difference between the two readings was 1.48 percent which is well within the acceptable range for the rod. Also, as shown in FIG. 2, the total counts of acoustic occurrences is 831 which, while high, is within the acceptable range. In contrast, the modulus of elasticity in FIG. 3 when calculated over the same relative load ranges provided readings of 6.69 $10^6$ psi and 6.042 $10^6$ psi for a percentage difference of 7.07 percent. This is too high and the rod should be rejected even though the count of acoustic occurrences is a very low 64. The change in the modulus of elasticity over the two load ranges indicates that the end fittings are not properly attached to the rod and the rod will probably fail in service by the failure of the end fittings.

The numbers given for acoustical counts and actual change of modulus of elasticity are good only for one particular rod system manufactured by one company. Other rods and manufacturers will have different numbers that must be arrived at by reasuring a sufficient number of rods to define a statistical distribution of the information.

What is claimed is:

1. A method for testing the overall quality of a fiberglass sucker rod having a known ultimate strength, comprising:
    applying tension loads that are less than said known ultimate strength to the end fittings of such a rod,
    measuring the applied loads and elongation for such a rod,
    measuring the acoustic emissions from such a rod during said applying of said tension loads,
    determining from said measured loads and elongation the modulus of elasticity for at least two different load ranges, and
    determining from the difference between said moduli of elasticity whether said end fittings of such a rod are acceptably attached and from said measured acoustic emissions whether the material of such a rod is acceptable.

2. The method of claim 1, wherein said difference between said moduli of elasticity is less than five percent for an acceptable rod.

3. The method of claim 2, further comprising:
    comparing said measured acoustical emissions with a statistically determined number to determine if such a rod is acceptable.

* * * * *